(12) United States Patent
Zarembo et al.

(10) Patent No.: US 8,364,282 B2
(45) Date of Patent: Jan. 29, 2013

(54) LEAD ASSEMBLY INCLUDING A POLYMER INTERCONNECT AND METHODS RELATED THERETO

(75) Inventors: Paul E. Zarembo, Vadnais Heights, MN (US); Elliott Rodriquez Roman, Vega Alta, PR (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/006,156

(22) Filed: Jan. 13, 2011

(65) Prior Publication Data

US 2011/0112616 A1 May 12, 2011

Related U.S. Application Data

(63) Continuation of application No. 11/468,996, filed on Aug. 31, 2006, now Pat. No. 7,917,229.

(51) Int. Cl.
*A61N 1/00* (2006.01)
(52) U.S. Cl. ......................................... 607/116; 607/122
(58) Field of Classification Search .................. 607/119, 607/122
See application file for complete search history.

(56) References Cited

U.S. PATENT DOCUMENTS

| | | | |
|---|---|---|---|
| 3,474,791 A | 10/1969 | Bentov | |
| 4,280,511 A | 7/1981 | O'Neill | |
| 4,379,462 A | 4/1983 | Borkan et al. | |
| 4,381,014 A | 4/1983 | Sandstrom et al. | |
| 4,484,586 A | 11/1984 | McMickle et al. | |
| 4,573,481 A | 3/1986 | Bullara | |
| 4,592,372 A | 6/1986 | Beranek | |
| 4,628,934 A | 12/1986 | Pohndorf et al. | |
| 4,643,202 A | 2/1987 | Roche | |
| 4,711,027 A | 12/1987 | Harris | |
| 4,721,115 A | 1/1988 | Owens | |
| 4,934,049 A | 6/1990 | Kiekhafer et al. | |
| 5,007,435 A | 4/1991 | Doan et al. | |
| 5,016,646 A | 5/1991 | Gotthardt et al. | |
| 5,016,808 A | 5/1991 | Heil, Jr. et al. | |
| 5,017,740 A | 5/1991 | Honkomp et al. | |
| 5,076,270 A | 12/1991 | Stutz, Jr. | |
| 5,115,818 A | 5/1992 | Holleman et al. | |
| 5,170,802 A | 12/1992 | Mehra | |
| 5,217,027 A | 6/1993 | Hermens | |
| 5,224,491 A | 7/1993 | Mehra | |
| 5,231,996 A | 8/1993 | Bardy et al. | |
| 5,350,419 A | 9/1994 | Bendel et al. | |
| 5,363,861 A | 11/1994 | Edwards et al. | |
| 5,368,564 A | 11/1994 | Savage | |
| 5,387,233 A | 2/1995 | Alferness et al. | |
| 5,423,865 A | 6/1995 | Bowald et al. | |
| 5,431,683 A | 7/1995 | Bowald et al. | |
| 5,458,629 A | 10/1995 | Baudino et al. | |
| 5,466,253 A | 11/1995 | Doan | |
| 5,476,498 A | 12/1995 | Ayers | |
| 5,483,022 A | 1/1996 | Mar | |
| 5,522,872 A | 6/1996 | Hoff | |

(Continued)

OTHER PUBLICATIONS

"U.S. Appl. No. 11/462,479 Advisory Action mailed Mar. 3, 2008", 3 pgs.

(Continued)

*Primary Examiner* — Nicole F Lavert
(74) *Attorney, Agent, or Firm* — Faegre Baker Daniels LLP

(57) ABSTRACT

A lead assembly includes a ring component having mechanical coupling features, and at least one polymer component mechanically coupled with the mechanical coupling features of the ring component. Elongate tubing is disposed over the polymer component and is secured with the polymer component.

16 Claims, 8 Drawing Sheets

U.S. PATENT DOCUMENTS

| | | | |
|---|---|---|---|
| 5,545,203 | A | 8/1996 | Doan |
| 5,549,642 | A | 8/1996 | Min et al. |
| 5,555,883 | A | 9/1996 | Avitall |
| 5,649,974 | A | 7/1997 | Nelson et al. |
| 5,676,694 | A | 10/1997 | Boser et al. |
| 5,741,319 | A | 4/1998 | Woloszko et al. |
| 5,766,527 | A | 6/1998 | Schidgen et al. |
| 5,792,217 | A | 8/1998 | Camps et al. |
| 5,796,044 | A | 8/1998 | Cobian et al. |
| 5,823,955 | A | 10/1998 | Kuck et al. |
| 5,845,396 | A | 12/1998 | Altman et al. |
| 5,853,652 | A | 12/1998 | Schildgen et al. |
| 5,871,531 | A | 2/1999 | Struble |
| 5,954,759 | A | 9/1999 | Swoyer et al. |
| 5,957,966 | A | 9/1999 | Schroeppel et al. |
| 6,047,217 | A | 4/2000 | Uhrberg |
| 6,055,457 | A | 4/2000 | Bonner |
| 6,083,216 | A | 7/2000 | Fischer, Sr. |
| 6,129,750 | A | 10/2000 | Tockman et al. |
| 6,161,029 | A | 12/2000 | Spreigl et al. |
| 6,181,971 | B1 | 1/2001 | Doan |
| 6,256,541 | B1 | 7/2001 | Heil et al. |
| 6,256,542 | B1 | 7/2001 | Marshall et al. |
| 6,289,251 | B1 | 9/2001 | Huepenbecker et al. |
| 6,301,507 | B1 | 10/2001 | Bakels et al. |
| 6,321,123 | B1 | 11/2001 | Morris et al. |
| 6,324,415 | B1 | 11/2001 | Spehr et al. |
| 6,363,288 | B1 | 3/2002 | Bush et al. |
| 6,366,820 | B1 | 4/2002 | Doan et al. |
| 6,374,476 | B1 | 4/2002 | Ponzi et al. |
| 6,430,449 | B1 | 8/2002 | Hsu et al. |
| 6,434,430 | B2 | 8/2002 | Borgersen et al. |
| 6,456,888 | B1 | 9/2002 | Skinner et al. |
| 6,456,890 | B2 | 9/2002 | Pianca et al. |
| 6,477,427 | B1 | 11/2002 | Stolz et al. |
| 6,500,174 | B1 | 12/2002 | Maguire et al. |
| 6,501,990 | B1 * | 12/2002 | Sundberg et al. ............. 607/122 |
| 6,501,991 | B1 | 12/2002 | Honeck et al. |
| 6,516,232 | B2 | 2/2003 | Skinner |
| 6,567,704 | B2 | 5/2003 | Sundquist et al. |
| 6,580,949 | B1 | 6/2003 | Tsuboi et al. |
| 6,584,362 | B1 | 6/2003 | Scheiner et al. |
| 6,611,720 | B2 | 8/2003 | Hata et al. |
| 6,650,945 | B2 | 11/2003 | Helland et al. |
| 6,669,691 | B1 | 12/2003 | Taimisto |
| 6,697,675 | B1 | 2/2004 | Safarevich et al. |
| 6,721,598 | B1 | 4/2004 | Helland et al. |
| 6,748,277 | B1 | 6/2004 | Chitre et al. |
| 6,757,970 | B1 | 7/2004 | Kuzma et al. |
| 6,801,809 | B2 | 10/2004 | Laske et al. |
| 6,843,870 | B1 | 1/2005 | Bluger |
| 6,879,861 | B2 | 4/2005 | Benz et al. |
| 6,882,886 | B1 | 4/2005 | Witte et al. |
| 6,895,277 | B2 | 5/2005 | Westlund et al. |
| 6,912,423 | B2 | 6/2005 | Ley et al. |
| 6,915,169 | B2 | 7/2005 | Flynn et al. |
| 6,968,236 | B2 | 11/2005 | Hagele |
| 6,978,185 | B2 | 12/2005 | Osypka |
| 6,983,185 | B2 | 1/2006 | Ley et al. |
| 7,013,182 | B1 | 3/2006 | Krishnan |
| 7,917,229 | B2 | 3/2011 | Zarembo et al. |
| 2002/0082651 | A1 | 6/2002 | Stahmann et al. |
| 2002/0107551 | A1 | 8/2002 | Stahmann et al. |
| 2002/0143377 | A1 | 10/2002 | Wessman et al. |
| 2003/0036779 | A1 | 2/2003 | Westlund et al. |
| 2003/0040787 | A1 | 2/2003 | Flynn et al. |
| 2003/0069625 | A1 | 4/2003 | Ley et al. |
| 2003/0074031 | A1 | 4/2003 | Ley et al. |
| 2003/0105505 | A1 | 6/2003 | Pianca |
| 2003/0139794 | A1 | 7/2003 | Jenney et al. |
| 2003/0153967 | A1 | 8/2003 | Koblish et al. |
| 2003/0204229 | A1 | 10/2003 | Stokes |
| 2003/0204230 | A1 | 10/2003 | Yang et al. |
| 2004/0064173 | A1 | 4/2004 | Hine et al. |
| 2004/0064174 | A1 | 4/2004 | Belden et al. |
| 2004/0093052 | A1 * | 5/2004 | Westlund et al. ............. 607/116 |
| 2004/0172116 | A1 | 9/2004 | Seifert et al. |
| 2004/0260371 | A1 | 12/2004 | Greenland et al. |
| 2004/0260374 | A1 | 12/2004 | Zhang et al. |
| 2004/0260375 | A1 | 12/2004 | Zhang et al. |
| 2005/0004642 | A1 | 1/2005 | Shoberg |
| 2005/0010095 | A1 | 1/2005 | Stewart et al. |
| 2005/0027339 | A1 | 2/2005 | Schrom et al. |
| 2005/0027340 | A1 | 2/2005 | Schrom et al. |
| 2005/0027341 | A1 | 2/2005 | Schrom et al. |
| 2005/0027343 | A1 | 2/2005 | Westlund et al. |
| 2005/0084672 | A1 | 4/2005 | O'Brien |
| 2005/0095892 | A1 | 5/2005 | Fukuyama |
| 2005/0202703 | A1 | 9/2005 | Westlund et al. |
| 2005/0227398 | A1 | 10/2005 | Anderson et al. |
| 2005/0228469 | A1 | 10/2005 | Zarembo et al. |
| 2005/0234522 | A1 | 10/2005 | Ley et al. |
| 2005/0267557 | A1 | 12/2005 | Flynn et al. |
| 2006/0015164 | A1 | 1/2006 | Partridge et al. |
| 2006/0036307 | A1 | 2/2006 | Zarembo et al. |
| 2006/0089698 | A1 | 4/2006 | Sundberg et al. |
| 2006/0100711 | A1 | 5/2006 | Cauthen |
| 2006/0129220 | A1 | 6/2006 | Koop et al. |
| 2006/0241734 | A1 | 10/2006 | Marshall et al. |
| 2006/0259106 | A1 | 11/2006 | Arnholt et al. |
| 2007/0055334 | A1 | 3/2007 | Haldeman et al. |
| 2007/0066998 | A1 | 3/2007 | Hansen et al. |
| 2007/0168004 | A1 | 7/2007 | Walter |
| 2007/0250144 | A1 | 10/2007 | Falk et al. |
| 2007/0255378 | A1 | 11/2007 | Polkinghorne et al. |
| 2008/0046059 | A1 | 2/2008 | Zarembo et al. |
| 2008/0057784 | A1 | 3/2008 | Zarembo et al. |

OTHER PUBLICATIONS

"U.S. Appl. No. 11/462,479 Response filed Mar. 11, 2008 to Advisory Action mailed Mar. 3, 2008", 18 pgs.

"U.S. Appl. No. 11/462,479 Response filed Feb. 11, 2008 to Final Office Action mailed Dec. 11, 2007", 19 pages.

"U.S. Appl. No. 11/462,479 Response filed Mar. 11, 2008 to Final Office Action mailed Dec. 11, 2008 and Advisory Action mailed Mar. 3, 2008".

U.S. Appl. No. 11/468,996, Response filed Jan. 17, 2008 to Restriction Requirement mailed Dec. 17, 2007, 8 pgs.

U.S. Appl. No. 11/468,996, Response filed Aug. 10, 2009 to Final Office Action mailed, Apr. 9, 2009, 9 pages.

"U.S. Appl. No. 11/468,996, Restriction Requirement mailed Dec. 17, 2007", 9 pgs.

U.S. Appl. No. 11/468,996m Response filed May 27, 2008 to Non-Final Office Action mailed Feb. 26, 2008, 9 pgs.

U.S. Appl. No. 11/468,996, Non-Final Office Action mailed Oct. 6, 2008, 8 pages.

U.S. Appl. No. 11/468,996, Non-Final Office Action mailed Feb. 26, 2008, 14 pgs.

Hansen, David J . et al., "Multi-Site Lead/System Using a Multi-Pole Connection and Methods Therefor". U.S. Appl. No. 11/230,989, filed Sep. 20, 2005, 55 pages.

Zarembo, Paul E. et al., "Lead Assembly Including a Polymer Interconnect and Methods Related Thereto", U.S. Appl. No. 11/468,996, filed Aug. 31, 2006, 23 Pages.

"U.S. Appl. No. 11/468,996, Response filed Jan. 6, 2009 to Non-Final Office Action mailed Oct. 6, 2008", 9 pages.

"U.S. Appl. No. 11/468,996, Final Office Action mailed Apr. 9, 2009", 8 pages.

Zarembo, Paul E. et al., "Interconnections of Implantable Lead Conductors and Electrodes and Reinforcement Therefor", U.S. Appl. No. 11/305,925, filed Dec. 19, 2005.

* cited by examiner

LEAD ASSEMBLY INCLUDING A POLYMER INTERCONNECT AND METHODS RELATED THERETO

RELATED APPLICATIONS

This application is a continuation of U.S. patent application Ser. No. 11/468,996, filed on Aug. 31, 2006, now U.S Pat. No. 7,917,229, entitled "Lead Assembly Including a Polymer Interconnect and Methods Related Thereto," which is incorporated herein by reference in its entirety for all purposes.

Additionally, this application is related to U.S. patent application Ser. No. 11/462,479, filed on Aug. 4, 2006, now published as U.S. Publication No. 2008/0046059, entitled "Lead Including A Heat Fused or Formed Lead Body," assigned to a common assignee, and is hereby incorporated by reference in its entirety for all purposes.

TECHNICAL FIELD

Leads for linking medical devices with selected bodily tissue to be sensed or stimulated by such devices. More particularly, but not by way of limitation, this relates to a lead including a polymer interconnect and methods related thereto.

BACKGROUND

Leads represent the electrical link between an implantable medical device (referred to as "IMD"), such as a pacer or defibrillator, and a subject's cardiac or other bodily tissue, which is to be sensed or stimulated. A lead generally includes a lead body that contains one or more electrical conductors extending from a proximal end portion of the lead to an intermediate or distal end portion of the lead. The lead body includes insulating material for covering and electrically insulating the electrical conductors. The proximal end of the lead further includes an electrical connector assembly couplable with the IMD, while the intermediate or distal end portions of the lead include one or more electrodes that may be placed within or near a desired sensing or stimulation site within the body of the subject.

Implantable leads, such as those used for cardiac sensing or stimulation, should have the ability to remain fully assembled and leak resistant despite constant flexing or bending, which may be encountered with each ventricular or atrial contraction of cardiac tissue (within which the lead is implanted or near) or axial forces applied to the lead during implantation, repositioning, or lead extraction. In addition, implantable leads should be designed to resist failure due to extended contact with in vivo bodily fluids, such as blood.

What is needed is a lead having interconnects able to withstand axial forces disposed to the lead. What is further needed is a lead having interconnects that are capable of being manufactured without the use of adhesive.

BRIEF DESCRIPTION OF THE DRAWINGS

In the drawings, like numerals describe substantially similar components throughout the several views. The drawings illustrate generally, by way of example, but not by way of limitation, the various embodiments discussed herein.

DETAILED DESCRIPTION

The following detailed description includes references to the accompanying drawings, which form a part of the detailed description. The drawings show, by way of illustration, specific embodiments in which the present leads and methods may be practiced. These embodiments, which are also referred to herein as "examples," are described in enough detail to enable those skilled in the art to practice the present leads and methods. The embodiments may be combined, other embodiments may be utilized or structural and logical changes may be made without departing from the scope of the present leads and methods. It is also to be understood that the various embodiments of the present leads and methods, although different, are not necessarily mutually exclusive. For example, a particular feature, structure or characteristic described in one embodiment may be included within other embodiments. The following detailed description is, therefore, not to be taken in a limiting sense and the scope of the present leads and methods are defined by the appended claims and their legal equivalents.

Figure 1:
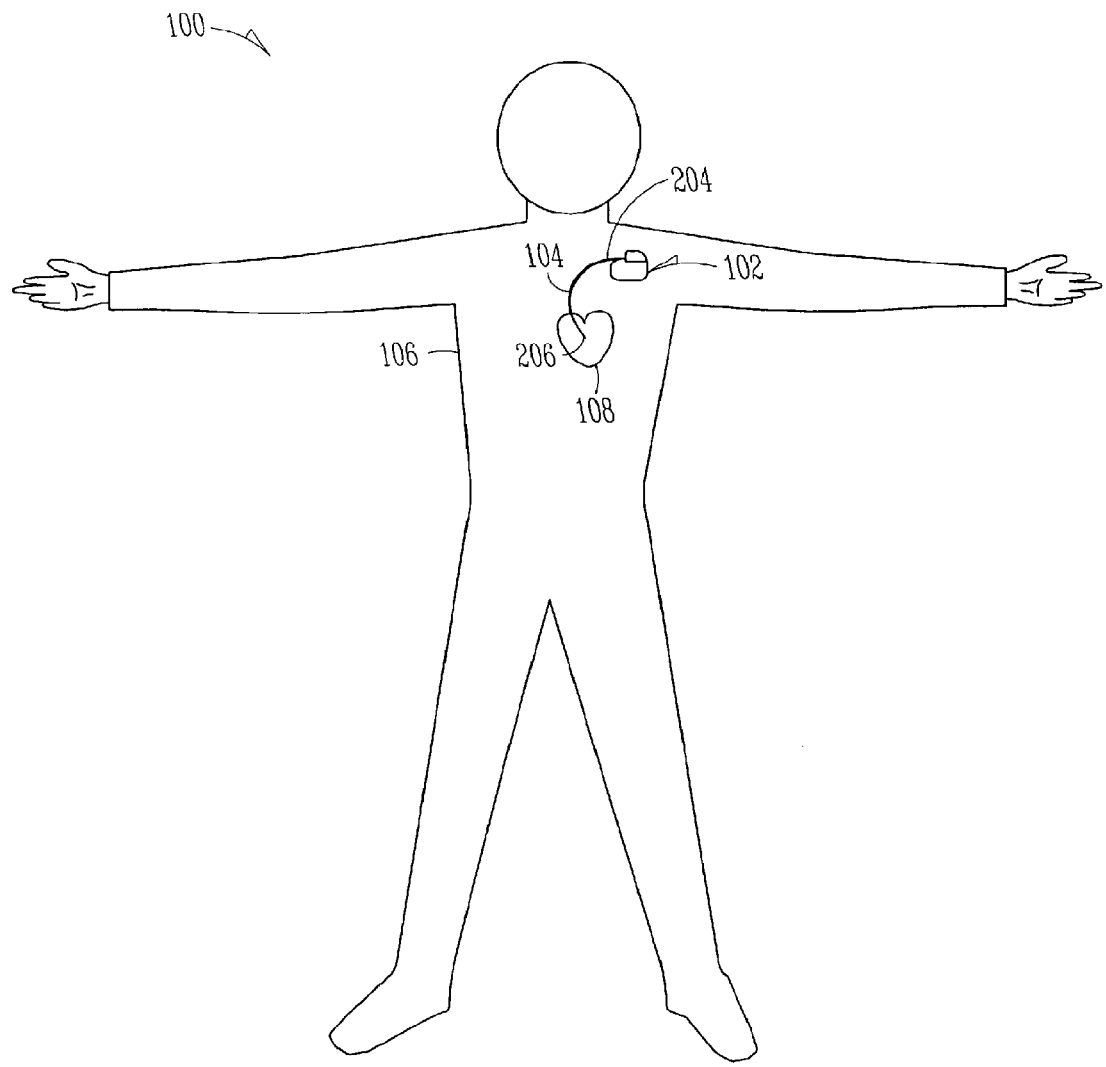
FIG. 1 is a schematic view illustrating an implantable lead system and an environment in which the lead system may be used, as constructed in accordance with at least one embodiment.

FIG. 1 illustrates a lead system 100 and an environment 106 (e.g., a subcutaneous pocket made in the wall of a subject's chest, abdomen, or elsewhere) in which the lead system 100 may be used. In varying examples, the lead system 100 may be used for delivering or receiving electrical pulses or signals to stimulate or sense a heart 108 of a patient. As shown in FIG. 1, the lead system 100 includes an IMD (implantable medical device) 102 and an implantable lead 104. The IMD 102 generically represents, but is not limited to, cardiac function management (referred to as "CFM") systems such as pacers, cardioverters/defibrillators, pacers/defibrillators, biventricular or other multi-site resynchronization or coordination devices such as cardiac resynchronization therapy (referred to as "CRT") devices, sensing instruments, or drug delivery systems.

Among other things, the IMD 102 includes a source of power as well as an electronic circuitry portion. In one example, the electronic circuitry includes microprocessors to provide processing, evaluation, and to determine and deliver electrical shocks or pulses of different energy levels and timing for ventricular defibrillation, cardioversion, or pacing of heart 108 in response to sensed cardiac arrhythmia including fibrillation, tachycardia, or bradycardia. In another example, the IMD 102 is a battery-powered device that senses intrinsic signals of the heart 108 and generates a series of timed electrical discharges.

The lead 104 includes a lead body 202 (FIG. 2A) extending from a lead proximal end portion 204, where it is couplable with the IMD 102. The lead 104 extends to a lead distal end portion 206, which is positioned within, on, or near tissue to be stimulated, such as a heart 108. The lead 104 further includes at least one electrode 116 (FIG. 2A) that electrically links the lead 104 with the heart 108.

At least one conductor 120 (FIG. 2A) is disposed within the lead body 202 and electrically couples the at least one electrode 116 with a terminal end of the lead 104 at the lead proximal end portion 204 and the IMD 102.

Figure 2A:
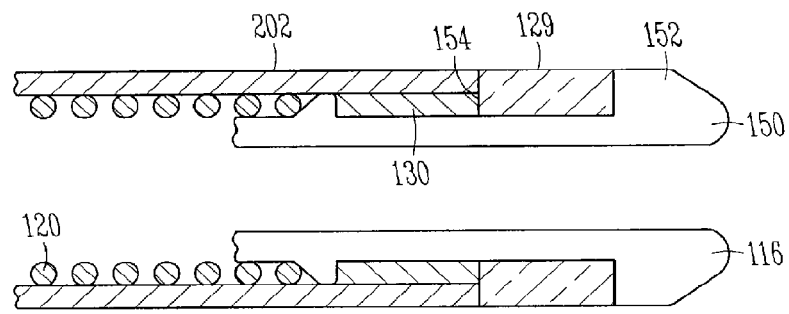
FIG. 2A is a cross-sectional view of a portion of a lead as constructed in accordance with at least one embodiment.

FIG. 2A illustrates an example of a distal portion of the lead 104 in greater detail. The lead 104 includes at least one polymer component 130 that is mechanically coupled with a ring component 150, and allows for a lead interconnection without the requirement of adhesive, although it is possible to use the interconnect with an adhesive. The ring component 150 includes, but is not limited to, a generally cylindrical ring component. It should be noted more than one polymer component 130 can be provided for additional joint integrity (see FIGS. 2C and 11). An optional drug eluting steroid collar 129 is provided adjacent to the ring component 150.

Figure 3:
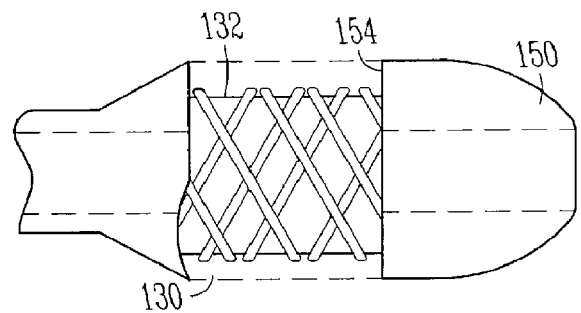
FIG. 3 is a side view of a portion of a lead as constructed in accordance with at least one embodiment.

The polymer component 130 includes a polymer ring, such as a ring formed of a thermoplastic, such as polyurethane, in an example. The polymer component 130 includes features that allow for the polymer component 130 to be mechanically coupled with the ring component 150 at an interface 132 (FIG. 3). For example, the polymer component 130 can be coupled with the ring component 150 with a snap fit coupling or an interference fit. In another option, the polymer component 130 is overmolded on to the ring component 150. In another option, the polymer component 130 is co-extruded, or coated on to the ring component 150, or coated on to tubing and placed on the ring component 150. In another option, the polymer component 130 is heat shrunk within a groove of the ring component. In yet another option, the polymer component 130 includes anti-torque features, such as, assisting in preventing movement of the polymer component 130 relative to the ring component 150. Optionally, the polymer component 130 has a lower melting point than the ring component 150.

Figure 2B:
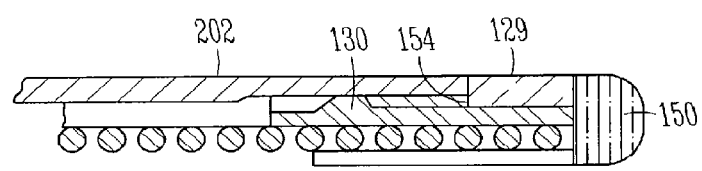
FIG. 2B is a cross-sectional view of a portion of a lead as constructed in accordance with at least one embodiment.
Figure 2B:
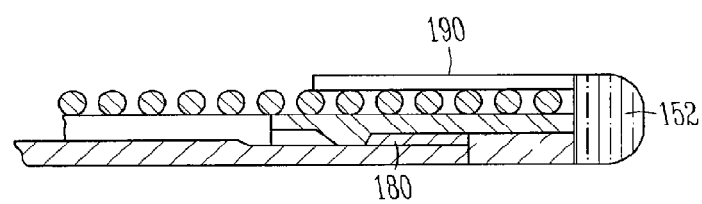
Figure 2C:
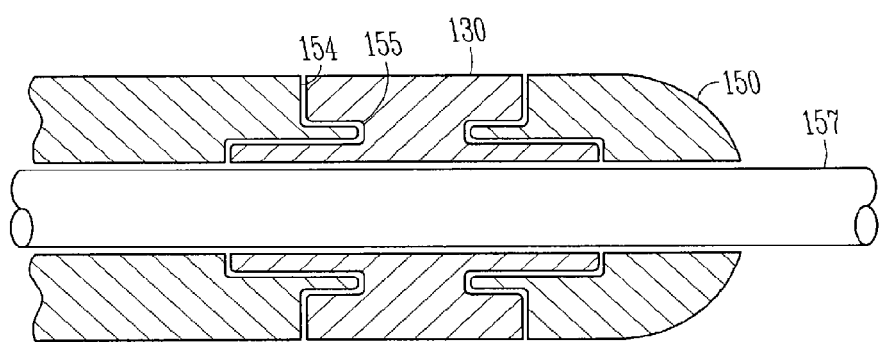
FIG. 2C is a cross-sectional view of a portion of a lead as constructed in accordance with at least one embodiment.

The polymer component 130 is disposed over the ring component 150. The ring component 150, in an option, is a metal component, for example, allowing for the ring component 150 to be used as a distal electrode 152 of the lead 104. In another option, the ring component 150 is formed in whole or in part of a higher melting point polymer (e.g. PEEK). In an option, the ring component 150 includes at least one recess 154, such as an annular recess, allowing for the polymer component to be received therein. Optionally, an inner metal tube 190 is disposed within the ring component 150, as shown in FIG. 2B. The optional inner metal tube 190 allows for the capture of, for example, coil filars and/or to size the lead lumen to allow a stylet to push the lead tip, and still allow guidewire passage. In another option as shown in FIG. 2C, at least one hole 155 is provided within the ring component 150, and optionally two polymer components are sandwiched around the at least one hole 155. When fused together, as discussed further below, the polymer components flow together through the hole 155. An optional mandrel 157 provides support for the inner polymer component.

Figure 4:
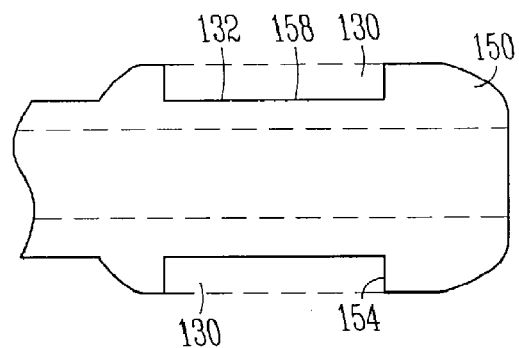
FIG. 4 is a side view of a portion of a lead as constructed in accordance with at least one embodiment.
Figure 5:
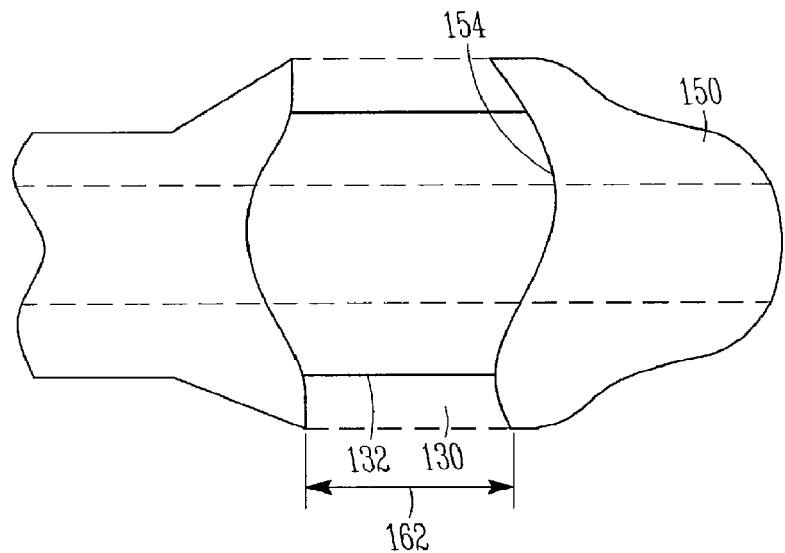
FIG. 5 is a side view of a portion of a lead as constructed in accordance with at least one embodiment.
Figure 6:
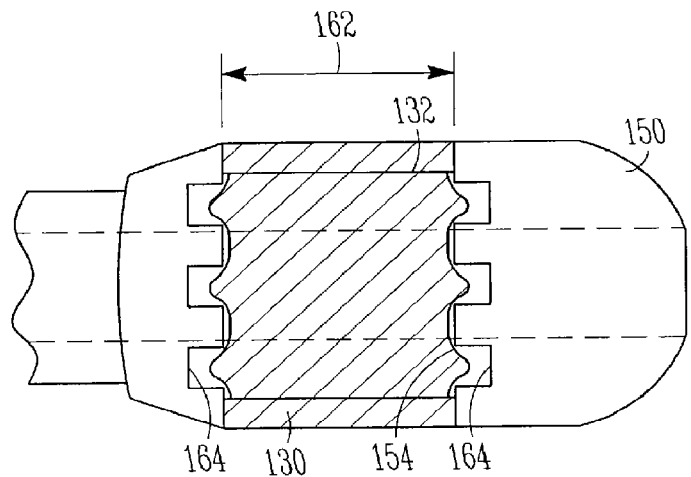
FIG. 6 is a side view of a portion of a lead as constructed in accordance with at least one embodiment.
Figure 7:
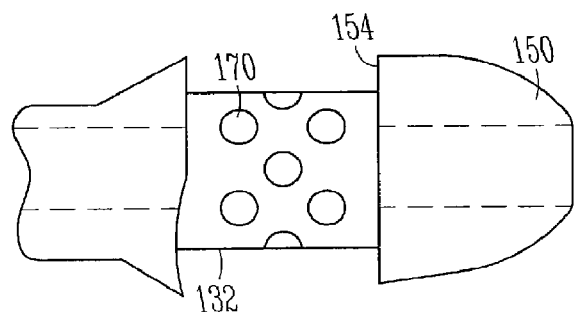
FIG. 7 is a side view of a portion of a lead as constructed in accordance with at least one embodiment.
Figure 8:
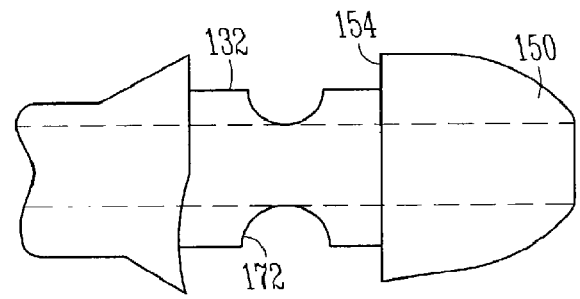
FIG. 8 is a side view of a portion of a lead as constructed in accordance with at least one embodiment.

FIGS. 3-8 illustrate additional options for the ring component 150, such as anti-torque features. For example, FIG. 3 illustrates a ring component 150 having a textured, substantially non-smooth surface at the interface 132, such as a knurled surface or a surface having cross-threads thereon. FIG. 4 illustrates another option for the ring component 150, where the ring component 150 includes a roughened surface 158. The textured surface can be formed by grit blasting or machining, for example. Additional options for providing non-smooth surfaces are illustrated in FIGS. 7 and 8. For example, the ring component 150 includes one or more holes 170 formed within the recess, as shown in FIG. 7, or one or more slots 172 formed within the recess, as shown in FIG. 8.

The ring component 150 includes mechanical coupling and/or anti-torque features, such as the recess 154, allowing for the polymer component 130 to be coupled therewith. FIGS. 5 and 6 illustrate additional options in which the recess 154 has a varying width 162. For instance, in FIG. 5, the width varies around the perimeter of the ring component 150. FIG. 6 illustrates another option wherein the recess 154 includes one or more teeth 164. The one or more teeth 164 allow for the polymer component 130 to deform within the teeth 164, providing for additional strength for the interconnection. The teeth 164 allow for the width of the recess 154 to be varied around at least a portion of the perimeter of the ring component 150. The teeth 164 can have a variety of shapes such as, but not limited to, square, rectangular, triangular, circular, etc. These above-discussed features are formed on the ring component 150, for example, by machining the features thereon or therein.

Referring again to FIG. 2A, the polymer component 130 is mechanically coupled with the ring component 150, for example with ring component coupling features. Elongate tubing, such as the lead body, is disposed over the polymer component 130 and is coupled or secured therewith, for example by fusing. Suitable methods for fusing the polymer component 130 and the lead body 202 include, but are not limited to, applying energy to change the polymer component 130 including heat shrinking with heat and/or pressure, laser, inductive heat, or radio frequency, heat mandrel inside of joint, heated jaws, laser, or combinations thereof. This allows for a secure joint 180 (FIG. 2B) to be formed between the lead body 202 and the polymer component 130 without the need for adhesive.

Figure 9:
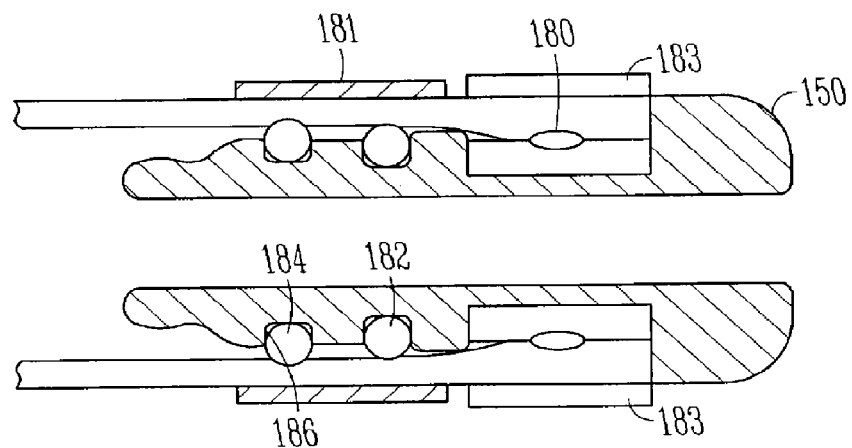
FIG. 9 is a cross-sectional view of a distal portion of the lead as constructed in accordance with at least one embodiment.
Figure 10:
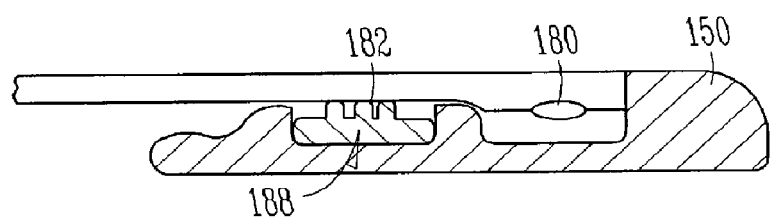
FIG. 10 is a cross-sectional view of a distal portion of the lead as constructed in accordance with at least one embodiment.
Figure 11:
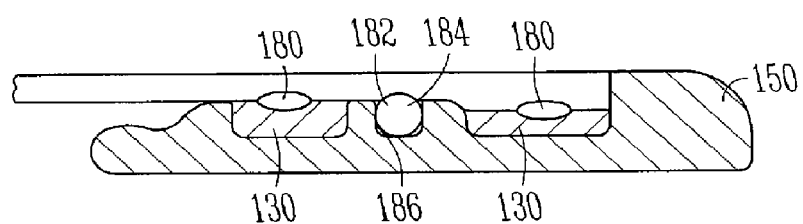
FIG. 11 is a cross-sectional view of a distal portion of the lead as constructed in accordance with at least one embodiment.

For additional sealing properties, an optional seal(s) 182 can be provided between the polymer component 130 and the ring component 150, as illustrated in FIGS. 9-11. For example, an O-ring 184 can be provided within recesses 186 of the ring component 150. In another example, an elastomer, such as an elastomer with a ribbed shape 188, can be provided within the recess 186, where the elastomer forms a seal between the ring component 150 and the polymer component 130. In another example, as shown in FIGS. 9 and 11, a joint 180 can be formed on one side of the seal 182, or on either side of the seal 182, providing for additional sealing integrity. In yet another option, an outer band 181, such as a metal band or polymer band, such as a band resistant to creep, is provided around the seal 182. In another option, an outer band 183, such as a metal band or polymer band, such as a band resistant to creep, is provided around the joint 180. The outer bands 181, 183 do not creep significantly, and assist with sealing integrity and increase axial joint strength. The outer bands 181, 183 can be swaged into place using a marker band swager or a rotary swager, for example, or welded or bonded in place.

Figure 12:
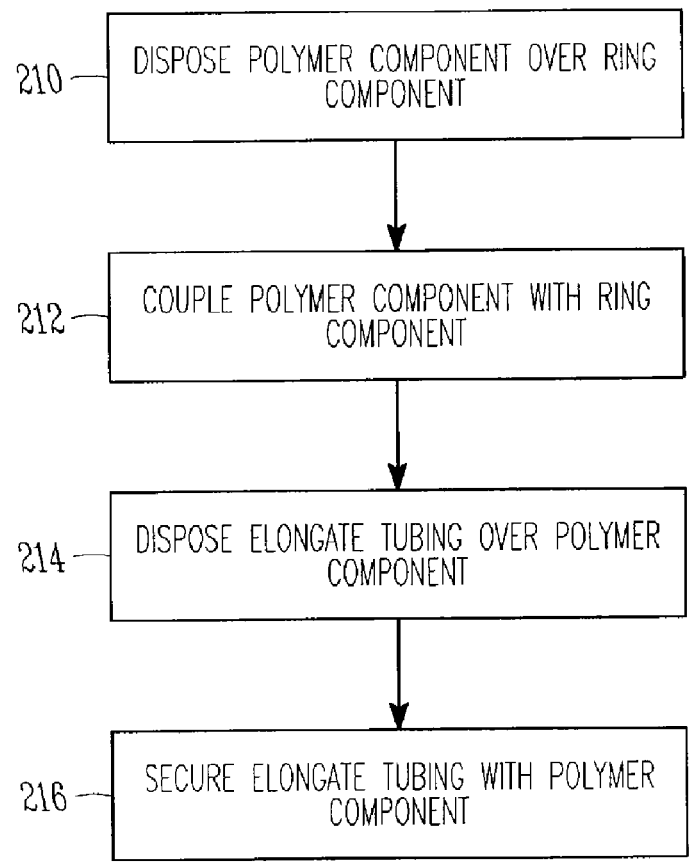
FIG. 12 is a flow chart for a method as constructed in accordance with at least one embodiment.

Referring to FIG. 12, to form the lead assembly, at 210, a polymer component 130 is disposed over the ring component 150, where the ring component 150 optionally includes mechanical coupling features, and at 212 the polymer component 130 is coupled with the ring component 150. In an example, the polymer component 130 is formed of polyurethane, and in an option having a durometer of 80A-80D. However, it should be noted that the polymer component 130 is not necessarily so limited.

Figure 13:
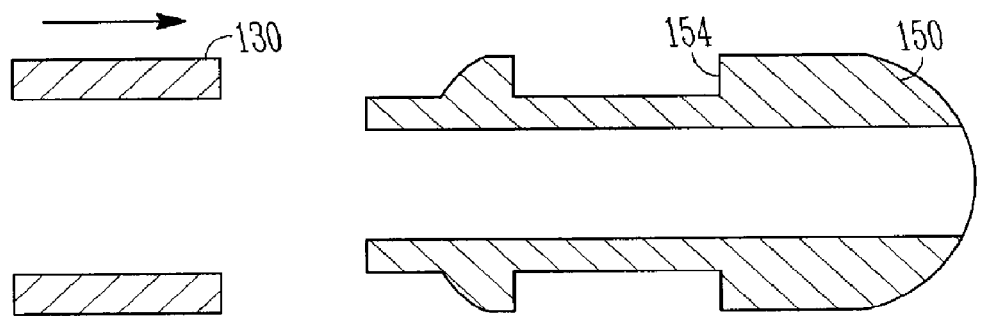
FIG. 13 is a cross-sectional view of a distal portion of the lead as constructed in accordance with at least one embodiment.
Figure 14:
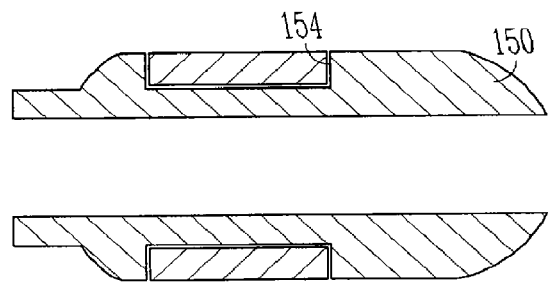
FIG. 14 is a cross-sectional view of a distal portion of the lead as constructed in accordance with at least one embodiment.

In an example illustrated in FIG. 13, the polymer component 130 is slid over the ring component 150, optionally over a ramp. In an option, the polymer component 130 is slid into the recess 154. In an option, the polymer component 130 is slid over the ring component 150 and into an interference fit with the ring component 150. In a further option, the ring component 150 and recess 154, and/or the polymer component 130 are sized such that the polymer component 130 fits in the recess 154 with a snap fit coupling, as shown in FIG. 14. In yet another option, the polymer component 130 is slid longitudinally or radially over the ring component 150 and is optionally not in an interference fit, and can optionally rotate around the component 150. In an example, the polymer component 130 is overmolded on to the ring component 150.

Figure 15:
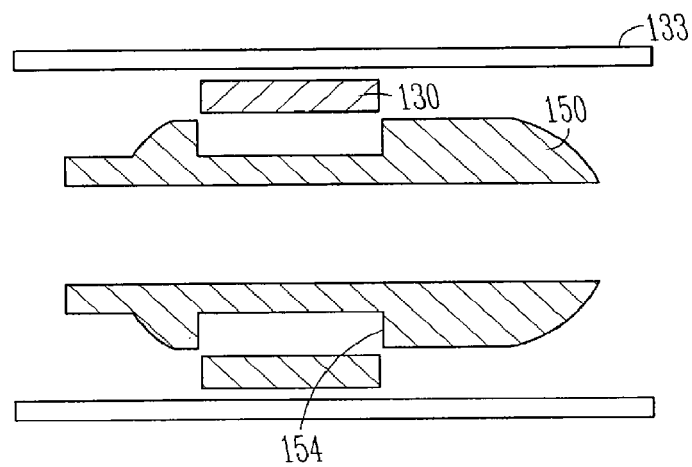
FIG. 15 is a cross-sectional view of a distal portion of the lead as constructed in accordance with at least one embodiment.

In another example, after the polymer component 130 is disposed over the recess 154, tubing 133, for example low density polyethylene or heat shrink tubing, is disposed over the polymer component 130, and is shrunk, for example while heating, to deform the polymer component 130 into the recess 154 of the ring component 150, as shown in FIG. 15. It should be noted that heat can be applied to the polymer component 130 and/or tubing 133 for example, but not limited to, by a laser, such as a CO2 laser, RF, oven, inductive heater, YAG laser, diode laser, alone or in combination with added pressure. The ring component 150 is optionally provided with textured portions, or holes such that the polymer component 130 can be shrunk on to the textured portions or through the holes to mate with a second polymer component.

Figure 16:
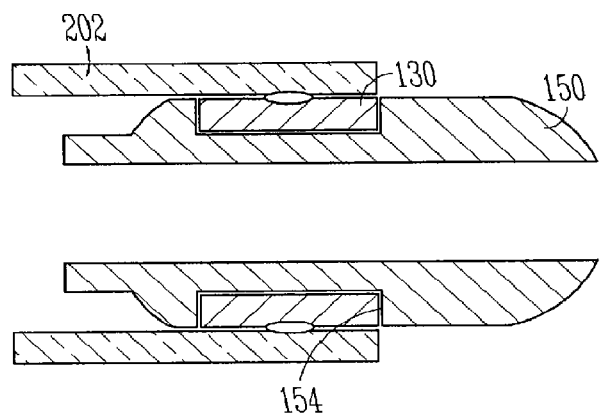
FIG. 16 is a cross-sectional view of a distal portion of the lead as constructed in accordance with at least one embodiment.

Referring again to FIG. 12, at 214 and 216, elongate tubing 202 is disposed over the polymer component 130, and the elongate tubing 202 is secured or coupled with the polymer component 130. Examples of the elongate tubing 202 include, but are not limited to, elastomeric thermoplastic, such as 55D polyurethane. In an option, the elongate tubing 202 and the polymer component 130 have similar melting points. The elongate tubing 202 is coupled or secured with the polymer component 130, as illustrated in FIG. 16. Example methods of securing or coupling at a joint include, but are not limited to, fusing with a laser, heat and/or pressure, or bonding with an adhesive.

Figure 17:
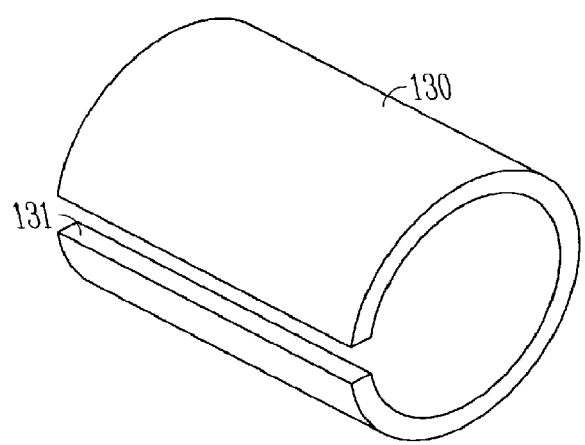
FIG. 17 is a perspective view of a polymer component as constructed in accordance with at least one embodiment.
Figure 18:
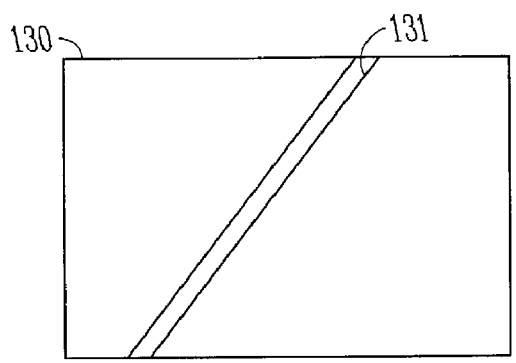
FIG. 18 is a side view of a polymer component as constructed in accordance with at least one embodiment.
Figure 19:
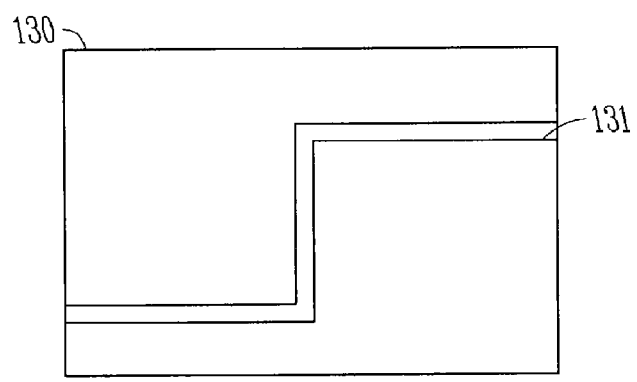
FIG. 19 is a side view of a polymer component as constructed in accordance with at least one embodiment.

FIGS. 17-19 illustrate additional options for the polymer component 130. The polymer component 130 includes a slitted portion 131 and/or an element that allows for the polymer component 130 to temporarily expand for installation, and contract to secure with the ring. The slitted portion 131 can have a variety of shapes, and extends in various ways radially and/or longitudinally. For example, the slitted portion 131 can extend substantially straight along a longitudinal portion, as shown in FIG. 17. Other examples includes FIGS. 18 and 19 shown a slitted portion extending in a helical shape, FIG. 18, or a stepped configuration, FIG. 19.

The lead system is further assembled. For example, one or more conductors are disposed within the elongate tubing, for example, by stringing. The one or more conductors are electrically coupled with one or more electrodes, such as the distal electrode ring component.

Advantageously, the joint provided between the ring component, the polymer component, and the elongate tubing can be made relatively quickly, and will not degrade over time, even in a wet environment or within a body.

It is to be understood that the above description is intended to be illustrative, and not restrictive. It should be noted that the above text discusses and figure illustrate, among other things, implantable leads for use in cardiac situations; however, the present leads and methods are not so limited. Many other embodiments and contexts, such as for non-cardiac nerve and muscle situations or for external nerve and muscle situations, will be apparent to those of skill in the art upon reviewing the above description. The scope should, therefore, be determined with reference to the appended claims, along with the full scope of legal equivalents to which such claims are entitled.

What is claimed is:

1. A lead assembly comprising:
   a lead body extending from a proximal end portion to a distal end portion, the distal end portion comprising an interconnect including a polymer ring component mechanically coupled to a generally cylindrical ring component having an outer surface, wherein a portion of an inner surface of the polymer ring component is disposed over and in contact with the outer surface of the generally cylindrical ring component;
   at least one conductor extending within the lead body from the proximal end portion in a direction toward the distal end portion; and
   at least one electrode operatively coupled to the at least one conductor.

2. The lead assembly according to claim 1, wherein the outer surface of the generally cylindrical ring component includes one or more mechanical coupling features.

3. The lead assembly according to claim 1, wherein the outer surface of the generally cylindrical ring component is a non-smooth, textured outer surface.

4. The lead assembly according to claim 1, wherein the generally cylindrical ring component comprises an annular recess defining a recessed outer surface and wherein at least a portion of the polymer ring component is disposed within the annular recess such that a portion of the inner surface of the polymer ring component is disposed over and in contact with the recessed outer surface of the generally cylindrical ring component.

5. The lead assembly according to claim 1, wherein the generally cylindrical ring component comprises a recessed portion defining a width and a recessed outer surface, wherein the width of the recessed portion varies around a perimeter of the ring component, and wherein a portion of the polymer ring component is disposed within the recessed portion of the generally cylindrical ring component such that an inner surface of the polymer ring component contacts the recessed outer surface of the generally cylindrical ring component.

6. The lead assembly according to claim 1, wherein the interconnect further comprises a seal disposed between the polymer ring component and the generally cylindrical ring component.

7. The lead assembly according to claim 1, wherein the generally cylindrical ring component forms the at least one electrode.

8. The lead assembly according to claim 7, wherein the at least one electrode is a distal tip electrode.

9. The lead assembly according to claim 1, wherein the generally cylindrical ring component comprises a recessed portion and one or more holes formed within the recessed portion.

10. The lead assembly according to clam 1, wherein the generally cylindrical ring component comprises a recessed portion and one or more slots formed within the recessed portion.

11. The lead assembly according to claim 1, wherein the lead body further comprises an elongate tube disposed over and in contact within at least a portion of the outer surface of the polymer ring component.

12. The lead assembly according to claim 1, wherein the generally cylindrical ring component is a generally cylindrical polymer ring component having a higher melting point temperature than the polymer ring component.

13. The lead assembly according to claim 1, wherein the generally cylindrical ring component is a metal ring component.

14. The lead assembly according to claim 1, wherein the generally cylindrical ring component comprises a ramp and wherein a portion of the polymer ring component is disposed over the ramp.

15. The lead assembly according to claim 1, wherein the generally cylindrical ring component comprises a recess and the polymer ring component is sized to fit within the recess.

16. The lead assembly according to claim 1, further comprising an inner metal tube disposed within the generally cylindrical ring component.

* * * * *